United States Patent [19]

Evans et al.

[11] Patent Number: 4,785,016
[45] Date of Patent: Nov. 15, 1988

[54] INDOLE DERIVATIVES

[75] Inventors: Brian Evans, Buntingford; Alexander W. Oxford, Royston; Darko Butain, Arlesey, all of England

[73] Assignee: Glaxo Group Limited, London, England

[21] Appl. No.: 804,102

[22] Filed: Dec. 3, 1985

[30] Foreign Application Priority Data

Dec. 4, 1984 [GB] United Kingdom ............... 84306424
Dec. 4, 1984 [GB] United Kingdom ................ 8430625
Dec. 4, 1984 [GB] United Kingdom ................ 8430626
Dec. 5, 1984 [GB] United Kingdom ................ 8430773

[51] Int. Cl.$^4$ .................... A61K 31/40; C07D 209/16
[52] U.S. Cl. ................................. 514/415; 514/211; 514/212; 514/218; 514/253; 514/256; 514/323; 514/374; 514/378; 514/385; 514/406; 514/414; 540/488; 540/492; 540/602; 544/63; 544/96; 544/143; 544/238; 544/333; 544/373; 546/201; 548/215; 548/240; 548/300; 548/356; 548/467; 548/504; 548/505

[58] Field of Search ............... 548/504, 506, 505, 467, 548/215, 356, 300, 240; 514/415, 414, 229, 323, 211, 212, 406, 385, 374, 253, 378, 218; 540/602, 488, 492; 544/373, 333, 238, 96, 63, 143; 546/201

[56] References Cited

U.S. PATENT DOCUMENTS 3,472,870 10/1969 Larsen et al. ...................... 548/504

FOREIGN PATENT DOCUMENTS 2150932 7/1985 United Kingdom ................ 548/504

Primary Examiner—Mary E. Ceperley
Attorney, Agent, or Firm—Bacon & Thomas

[57] ABSTRACT

Indole derivatives are disclosed of formula (I):

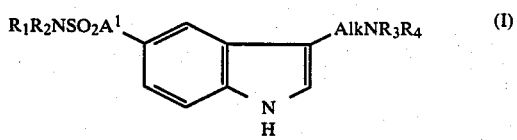

wherein
  $R_1$ represents H, alkyl or alkenyl;
  $R_2$ represents H, alkyl, alkenyl, cycloalkyl or phenyl or phenyl alkyl the phenyl ring being optionally substituted by halogen, alkyl, alkoxy, hydroxyl or by a group —$NR_aR_b$, or —$CONR_aR_b$, wherein $R_a$ and $R_b$ are H, alkyl, alkenyl, or with the nitrogen atom form a saturated monocyclic ring;
  $R_3$ and $R_4$ are H, alkyl or propenyl or together form an aralkylidene group;
  Alk represents a $Cf_{2-3}$ alkyl chain optionally substituted by one or two alkyl groups; and
  $A^1$ represents a $C_{2-5}$ alkenyl chain and salts and solvates thereof.

The compounds have selective vasoconstrictor activity and are useful in treating and/or preventing pain resulting from dilatation of the cranial vasculature, particularly migraine. The compounds may be formulated in conventional manner with pharmaceutically acceptable carriers or excipients. Various process for the preparation of the compounds (I) are disclosed.

8 Claims, No Drawings

INDOLE DERIVATIVES

This invention relates to indole derivatives, to processes for their preparation, to pharmaceutical compositions containing them and to their medical use, in particular to compounds and compositions of use in the treatment of migraine.

The pain of migraine is associated with excessive dilatation of the cranial vasculature and known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache, and a compound having a selective vasoconstrictor activity would fulfil such a role.

We have now found a group of indole derivatives having potent and selective vasoconstrictor activity.

The present invention provides indoles of the general formula (I):

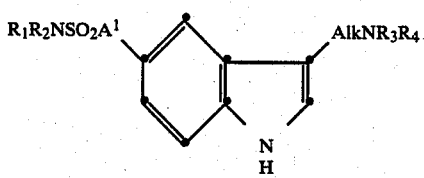

wherein $R_1$ represents a hydrogen atom or a $C_{1-6}$ alkyl or $C_{3-6}$ alkenyl group;

$R_2$ represents a hydrogen atom, a $C_{1-3}$ alkyl, $C_{3-6}$ alkenyl, or $C_{5-7}$ cycloalkyl group, or a phenyl or phenyl($C_{1-4}$)alkyl group in which the phenyl ring may be unsubstituted or substituted by a halogen atom, a $C_{1-3}$ alkyl, $C_{1-3}$ alkoxy or hydroxyl group, or by a group $-NR_aR_b$, or $-CONR_aR_b$, wherein $R_a$ and $R_b$, which may be the same or different, each represents a hydrogen atom or a $C_{1-3}$ alkyl or $C_{3-6}$ alkenyl group, or together with the nitrogen atom to which they are attached form a saturated monocyclic 5 to 7-membered ring, which may contain an additional hetero function, for example, an oxygen atom or the group $NR_5$ (where $R_5$ is a hydrogen atom or a lower alkyl group);

$R_3$ and $R_4$, which may be the same or different, each represents a hydrogen atom or a $C_{1-3}$ alkyl or propenyl group or $R_3$ and $R_4$ together form an aralkylidene group;

Alk represents an alkyl chain containing two or three carbon atoms which may be unsubstituted or substituted by not more than two $C_{1-3}$ alkyl groups; and $A^1$ represents an alkenyl chain containing two to five carbon atoms, and salts and solvents thereof.

All optical isomers of compounds of general formula (I) and their mixtures, including the racemic mixtures thereof, are embraced by the invention. The invention also includes within its scope geometric isomers of compounds (I) and mixtures of such isomers.

Referring to the general formula (I), the alkyl groups and the alkyl moiety of the alkoxy groups may be straight chain or branched chain alkyl groups containing 1 to 3 carbon atoms, or in the case of $R_1$, 1 to 6, preferably 1 to 3, carbon atoms. Examples of alkyl groups include methyl, ethyl, propyl and isopropyl groups. The alkenyl groups preferably contain 3 or 4 carbon atoms, examples of which include propenyl and butenyl groups. The cycloalkyl groups preferably contain 5 or 6 carbon atoms and examples include cyclopentyl and cyclohexyl groups. The alkyl moieties of the phenylalkyl groups preferably contain 1 or 2 carbon atoms as in e.g. benzyl and phenylethyl groups. The aralkylidene group is preferably an aryl methylidene group such as benzylidene. When $R_2$ represents a substituted phenyl or phenyl($C_{1-4}$)alkyl group the substituent may be in the ortho, meta or para positions. A halogen substituent on a phenyl ring in general formula (I) may be for example a fluorine, chlorine or bromine atom.

The alkenyl chain $A^1$ may for example, be represented by the formula

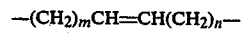

wherein m is zero or an integer from 1 to 3 and n is zero or an integer from 1 to 3, such that the sum of m and n together does not exceed 3.

When $R_2$ represents a substituted phenyl or phenyl($C_{1-4}$)alkyl group, m and n preferably each represent zero, 1 or 2, such that the sum of m and n together does not exceed 2.

It will be appreciated that the compounds of formula (I) may exist in the E- or Z-configuration with respect to the double bond in the alkenyl chain $-(CH_2)_mCH=CH(CH_2)_n-$. The present invention includes within its scope both isomeric forms as well as mixtures thereof. In general, compounds of the invention in the E-configuration are preferred. The E-configuration may be represented structurally as:

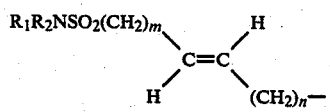

In the compounds of general formula (I), the alkenyl chain $A^1$ is preferably a group of formula:

wherein m is as previously defined, preferably zero or 1 and n is zero or 1, most preferably zero.

Thus, a preferred class of compounds according to the invention is that represented by general formula (I'):

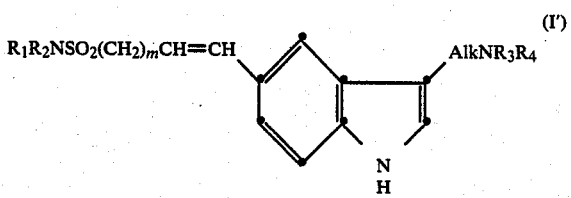

(wherein $R_1$, $R_2$, $R_3$, $R_4$, Alk and m are as previously defined) and physiologically acceptable salts and solvates (e.g. hydrates) thereof.

In the compounds of general formulae (I) and (I') Alk preferably represents an unsubstituted alkyl chain, especially an unsubstituted alkyl chain containing two carbon atoms.

$R_1$ is preferably a hydrogen atom or a $C_{1-6}$ alkyl group and $R_2$ preferably represents a hydrogen atom, a $C_{1-3}$ alkyl group, a $C_{5-7}$ cycloalkyl group or a substituted or unsubstituted phenyl or phenyl($C_{1-4}$)alkyl group. It is particularly preferred that one of $R_1$ or $R_2$ represents a hydrogen atom. When $R_2$ represents a substituted phenyl or phenyl($C_{1-4}$)alkyl group it is preferred that $R_1$ represents a hydrogen atom or a $C_{1-3}$ alkyl group.

Preferred substituents on the phenyl or phenyl($C_{1-4}$)alkyl group represented by $R_2$ are $C_{1-3}$ alkoxy groups and groups of the formula —$CONR_aR_b$ wherein $R_a$ and $R_b$, which may be the same or different each represents a hydrogen atom or a $C_{1-3}$ alkyl group.

$R_3$ and $R_4$, which may be the same or different preferably such represent a hydrogen atom or a $C_{1-3}$ alkyl group.

A particularly preferred class of compounds according to the invention is that represented by the general formula (Ia):

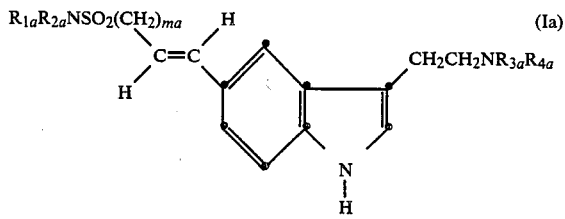

wherein
$R_{1a}$ represents a hydrogen atom or a $C_{1-3}$ alkyl group (e.g. methyl);
$R_{2a}$ represents a hydrogen atom, a $C_{1-3}$ alkyl group (e.g. methyl or ethyl) or a phenyl or phenyl($C_{1-2}$) alkyl group in which the phenyl ring is unsubstituted or substituted by a $C_{1-3}$ alkoxy group (e.g. methoxy) or by the group —$CONH_2$;
$R_{3a}$ and $R_{4a}$ each represents a hydrogen atom or a $C_{1-3}$ alkyl group (e.g. methyl); and
ma is zero or 1;
and physiologically acceptable salts and solvates (e.g. hydrates) thereof.

In the compounds of formula (Ia) it is preferred that the total number of carbon atoms in $R_{3a}$ and $R_{4a}$ does not exceed two, and most preferably $R_{3a}$ and $R_{4a}$ each represents a methyl group. In compounds (Ia) ma preferably represents zero.

Preferred compounds according to the invention:
(E)-2-[3-[2-(dimethylamino)ethyl]-1H-indol-5-yl]-N-methylethenesulphonamide;
(E)-2-[3-[2-(dimethylamino)ethyl]-1H-indol-5-yl]-N-(2-phenylethyl)ethenesulphonamide;
(E)-2-[3-[2-(dimethylamino)ethyl]-1H-indol-5-yl]-N-[(4methoxyphenyl)methyl]ethenesulphonamide;
and the physiologically acceptable salt and solvates (e.g. hydrates) of these compounds.

Suitable physiologically acceptable salts of the indoles of general formula (I) include acid addition salts formed with inorganic or organic acids, for example hydrochlorides, hydrobromides, sulphates, nitrates, phosphates, tartrates, citrates, fumarates, maleates, succinates, and sulphonates e.g. mesylates. Other salts of the indoles of general formula (I) include oxalates and creatinine sulphate adducts.

It will be appreciated that the invention extends to other physiologically acceptable equivalents of the compounds according to the invention, i.e. physiologically acceptable compounds which are converted in vivo into the parent compound. Examples of such equivalents include physiological acceptable, metabolically labile N-acyl derivatives.

Compounds of the invention potently and selectively constrict the carotid arterial bed of the anaesthetised dog, whilst having a negligible effect on blood pressure. The selective vasoconstrictor action of compounds of the invention has been demonstrated in vitro.

Compounds of general formula (I) are useful in treating and/or preventing pain resulting from dilatation of the cranial vasculature, in particular migraine and related disorders such as cluster headache.

Compounds of general formula (I') are preferred by virtue of their vasoconstrictor activity.

The invention also provides a pharmaceutical composition adapted for use in human medicine which comprises at least one compound according to the invention or a physiologically acceptable salt or solvate (e.g. hydrate) thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid). The liquid preparations may also contain conventional buffers, flavouring, colouring and sweetening agents as appropriate.

For buccal administration the compositions may take the form of tablets or lozenges formulated in conventional manner.

The compounds of the invention may be formulated for parenteral administration by injection or continuous infusion. Formulations for injection may be presented in unit dosage form e.g. in ampoules or in multi-dose containers, with an added preservative.

The compositions may take such forms as suspensions, solutions, or emulsions in oily or aqueous vehicles, and may contain formulatory agents such as suspending, stabilising and/or dispersing agents, and/or agents to adjust the tonicity of the solution. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a value to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral, buccal or rectal administration to man (of average bodyweight e.g. about 70 kg) for the treatment of migraine is 0.1 to 100 mg of the active ingredient per unit dose which could be administered, for example, up to 8 times per day, more usually 1 to 4 times per day. It will be appreciated that it may be necessary to make routine variations to the dosage depending on the age and weight of the patient as well as the severity of the condition to be treated.

For oral administration a unit dose will preferably contain from 0.5 to 50 mg e.g. 2 to 40 mg of the active ingredient. A unit dose for parenteral administration will preferably contain 0.2 to 5 mg of the active ingredient.

Aerosol formulations are preferably arranged so that each metered dose or 'puff' delivered from a pressurised aerosol contains 0.2 to 2 mg of a compound of the invention and, each dose administered via capsules or cartridges in an inhaler or insufflator contains 0.2 to 20 mg. The overall daily dose by inhalation will be within the range 1 mg to 100 mg. Administration may be several times daily, for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

In addition to their vasoconstrictor activity, compounds of general formula (I) are also useful as intermediates for the preparation of further indole derivatives. Thus, compounds of formula (I) may be reduced to give compounds of formula (II):

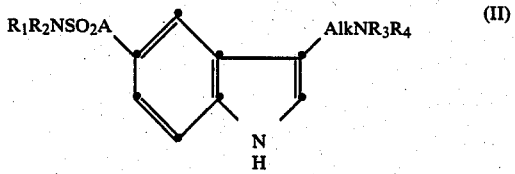
(II)

wherein $R_1$, $R_2$, $R_3$, $R_4$, and Alk are as previously defined, and A represents an alkyl chain containing two to five carbon atoms.

Compounds of formula (II) wherein $R_2$ represents a substituted phenyl or substituted phenyl($C_{1-4}$)alkyl group are described in our published European application No. 147107. Compounds of formula (II) wherein $R_2$ represents a hydrogen atom, a $C_{1-3}$ alkyl, $C_{3-6}$ alkenyl, or $C_{5-7}$ cycloalkyl group, or an unsubstituted phenyl or phenyl($C_{1-4}$)alkyl group are disclosed in our published UK application No. 2150932A.

The reduction of compounds of formula (I) to give compounds of formula (II) may be effected by methods well known in the art.

Thus, for example, a compound of formula (I) may be reduced by catalytic hydrogenation, using a heterogeneous or homogeneous catalyst. Heterogeneous catalysts which may be employed include Raney nickel; nickel reduced with sodium borohydride; and noble metal catalysts such as platinum, platinum oxide, palladium, palladium oxide, rhodium or ruthenium, which may be supported for example on charcoal, kieselguhr or alumina. In the case of Raney nickel, hydrazine may also be used as the source of hydrogen. Examples of homogeneous catalysts include chlorotris(triphenylphosphine)rhodium and pentacyano cobaltate. The catalytic hydrogenation may conveniently be carried out in a solvent such as an alcohol e.g. ethanol; an ether, e.g. dioxan or tetrahydrofuran, an amide, e.g. dimethylformamide; or an ester e.g. ethyl acetate, and at a temperature of from $-10°$ to $+50°$ C., preferably $-5°$ to $+30°$ C. The reaction may conveniently be effected at atmospheric pressure, but higher pressures, e.g. up to 5 atmospheres, may be employed.

The compounds of the present invention may also be reduced with other reducing agents such as sodium in ethanol, or sodium and t-butylalcohol in hexamethylphosphoramide, at a temperature of from 0° to 120° C.

The following compounds of general formula (II) which may be prepared from the corresponding compounds of formula (I) according to the above-described process, are novel compounds and constitute a further feature of the present invention:

3-[2-(dimethylamino)ethyl]-N-methyl-1H-indole-5-propanesulphonamide;

3-[2-(dimethylamino)ethyl]-N,N-dimethyl-1H-indole-5-ethanesulphonamide;

3-[2-(dimethylamino)ethyl]-N-(2-phenylethyl)-1H-indole-5-ethanesulphonamide;

3-[2-(dimethylamino)ethyl]-N-(1-methylethyl)-1H-indole-5-ethanesulphonamide;

3-[2-(dimethylamino)ethyl]-N-ethyl-1H-indole-5-ethanesulphonamide;

3-[(2-(dimethylamino)ethyl]-N-phenyl-1H-indole-5-ethanesulphonamide; and;

N-cyclopentyl-3-[2-(dimethylamino)ethyl]-1H-indole-5-ethane sulphonamide.

According to another aspect of the invention, compounds of general formula (I) and their salts and solvates may be prepared by the general methods outlined hereinafter. In the following processes $R_1$, $R_2$, $R_3$, $R_4$, $A^1$, Alk, m and n are as defined for the general formula (I) unless otherwise specified.

According to a general process (A), compounds of general formula (I) may be prepared by reacting an indole of general formula (III):

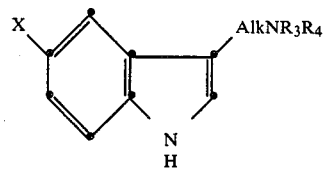

(wherein X represents a leaving atom or group such as a halogen atom, e.g. a bromine or iodine atom) with an alkene of formula (IV):

where $-A^2=CH_2$ represents a $C_{2-5}$ alkenyl chain.

The reaction will generally be effected in the presence of a palladium catalyst and a base. The catalyst may be for example palladium on charcoal or a palladium salt. Palladium salts which may be employed as catalysts include salts of organic acids, e.g. acetates, and salts of inorganic acids, e.g. chlorides or bromides. The base may be for example a tertiary nitrogen base such as triethylamine, or tri-n-butylamine or an alkali metal carbonate, e.g. sodium carbonate. The reaction may optionally be carried out in the presence of a phosphine, for example a triarylphosphine such as triphenylphosphine or tri-o-tolylphosphine. A phosphine should be present when the process is effected with a compound of formula (III) wherein X represents a bromine atom. The reaction is conveniently carried out using a small excess of the alkene (V) with respect to the indole (III). It is generally preferred that an excess of the base (e.g. ca. 3 equivalents) and, when present an excess of the phosphine (e.g. ca. 2 equivalents) are also employed.

General process (A) may be effected in the presence or absence of solvent. An anhydrous or aqueous reaction medium comprising one or more solvents may be employed. Suitable solvents include nitriles, e.g. acetonitrile; alcohols e.g. methanol or ethanol; amides e.g. dimethylformamide, N-methylpyrrolidone or hexamethylphosphoramide; and water. The reaction may conveniently be carried out at a temperature of from 25° to 200° C., preferably 75° to 150° C.

In the compounds of formula (IV) the moiety $-A^2=CH_2$ preferably represents the group $-(CH_2)_mCH=CH_2$, wherein m is zero or an integer from 1 to 3.

It will be appreciated that the compounds of formula (I) prepared by general process (A) will be those in which n is zero.

According to another general process (B) compounds of general formula (II) may be prepared by reacting an aldehyde of formula (V):

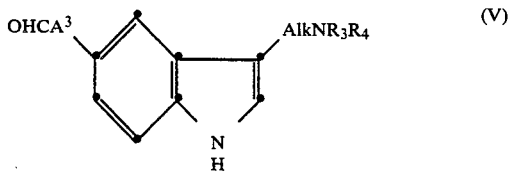

(wherein $A^3$ represents a bond or a $C_{1-3}$ alkyl chain) with a reagent serving to form the group $R_1R_2NSO_2A^1-$.

A suitable reagent serving to form the group $R_1R_2NSO_2A^1-$ may be, for example, a phosphorus ylide of general formula (VI):

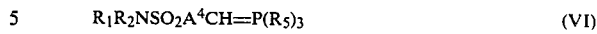

(wherein $A^4$ represents a bond or a $C_{1-3}$ alkyl chain such that the total number of carbon atoms in $A^3$ and $A^4$ does not exceed 3, and $R_5$ is an alkyl, e.g. methyl, or aryl, e.g. phenyl or tolyl group) or a phosphonate ester of general formula (VII):

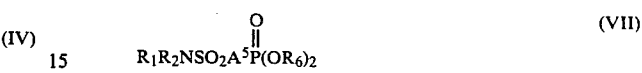

(wherein $A^5$ represents an alkyl chain containing 1 to 4 carbon atoms, such that the total number of carbon atoms in $A^3$ and $A^5$ does not exceed 4, $R_6$ represents an alkyl e.g. methyl; aryl e.g. phenyl or aralkyl e.g. benzyl group).

The reaction with an ylide of formula (VI) may conveniently be effected in an anhydrous reaction medium which may comprise one or more organic solvents. Solvents which may be employed include amides e.g. dimethylformamide; ethers, e.g. acrylic ethers such as diethylether and cyclic ethers such as tetrahydrofuran; and hydrocarbons e.g. xylene or toluene. The reaction may conveniently be conducted at a temperature of from $-70°$ to $+150°$ C.

A phosphonate ester of formula (VII) will preferably be reacted with an aldehyde of general formula (V) in the presence of a base, for example a metal hydride, such as sodium or potassium hydride; a metal amide such as sodium amide; an alkali metal alkoxide, such as potassium t-butoxide; or an organolithium base, such as butyllithium. The reaction may be conveniently effected in an organic reaction medium, which may comprise one or more solvents, and at a temperature in the range $-70°$ to $+150°$ C. Suitable solvents include amides, ethers and hydrocarbons, such as those mentioned above for the reaction with an ylide of formula (VI).

Phosphorus ylides of formula (VI) may be prepared by reaction of the corresponding phosphonium salt of formula (VIII):

(wherein $A^5$ and $R_5$ are as previously defined and $E^-$ represents an anion, such as a halide ion, e.g. a chloride, bromide or iodide ion; or a sulphonate anion, e.g. methanesulphonate or p-toluene sulphonate) with a base. Bases which may be employed include organolithium compounds e.g. n-butyllithium and phenyllithium; metal hydrides, e.g. sodium hydride; metal amides, e.g. sodium amide, alkali metal alkoxide e.g. sodium or potassium methoxide, ethoxide or t-butoxide; and alkali metal carbonates e.g. sodium carbonate. The formation of the phosphorus ylide may be effected in an organic solvent or mixture of solvents, for example as described for general process (B).

In a particular embodiment of general process (B), an aldehyde of general formula (V) may be reacted directly with a phosphonium salt of formula (VIII) in the presence of a base, using the reaction conditions described above for the reaction of an aldehyde (V) with an ylide of general formula (VI).

Compounds of formula (V) may be prepared by reacting a corresponding nitrile of formula (IX):

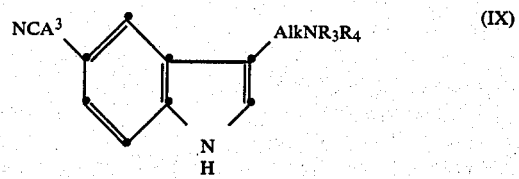

(wherein A³ is as previously defined for general formula (V)) with a reducing agent such as di-isobutylaluminium hydride, in a solvent such as tetrahydrofuran, followed by hydrolysis, which may be effected for example by the addition of water. The reaction may be effected at a temperature of −70° to 30° C.

Compounds of formula (IX) may be prepared by cyclisation of a corresponding hydrazone, in an analogous manner to process (D) described hereinafter.

Compounds of general formula (I) may also be prepared according to a further general process (C), which comprises elimination of HX¹ from a compound of formula (X):

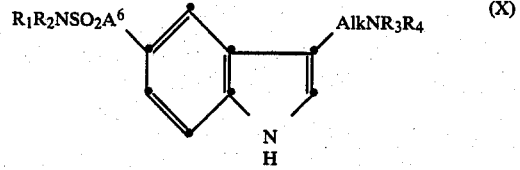

(wherein A⁶ represents a C₂₋₅ alkyl chain substituted by a leaving atom or group, X¹, for example a halogen atom, a hydroxy group or an acyloxy group).

The group A⁶ may for example be represented by the formula

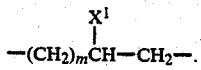

When X¹ in the group A⁶ represents a halogen atom, this may be, for example, bromine or chlorine. An acyloxy group X¹ may be derived from a carboxylic or sulphonic acid, such as an acetoxy, chloroacetoxy, p-nitrobenzoyloxy, p-toluenesulphonyloxy or methanesulphonyloxy group.

When X¹ represents a halogen atom or an acyloxy group, the elimination may be effected thermally, e.g. at a temperature of 30° to 200° C., or using a base such as an alkali metal alkoxide, e.g. sodium or potassium ethoxide or t-butoxide; an alkali metal hydroxide, e.g. sodium or potassium hydroxide; or a tertiary amine base e.g. triethylamine. The reaction with a base may be effected in an organic reaction medium, at a temperature in the range −10° to +150° C. Solvents which may be employed include alcohols e.g. ethanol or t-butanol; amides e.g. dimethylformamide; sulphoxides e.g. dimethylsulphoxide; halogenated hydrocarbons e.g. methylene chloride; ketones e.g. acetone and esters e.g. ethyl acetate, as well as mixtures of such solvents.

When X¹ represents a hydroxy group compounds of formula (X) may be heated with an acid such as sulphuric or phosphoric acid, to give a compound of formula (I).

Compounds of the formula (X) wherein X¹ represents an acyloxy group may be prepared for example by reacting the corresponding compound wherein X¹ is a hydroxyl group, with an appropriate acylating agent, such as an acid halide e.g. methanesulphonyl chloride. Compounds of formula (X) wherein X¹ represents a hydroxyl group may also be used to prepare corresponding compounds wherein X¹ is a halogen atom, for example, by reaction with the appropriate phosphorus trihalide.

Compounds of formula (X) wherein X¹ represents a hydroxyl group may themselves be prepared by condensing an aldehyde of general formula (V) with an appropriate alkane sulphonamide in the presence of a base such as n-butyllithium or lithium di-isopropylamine at temperatures of from −80° to −10° C.

A further general process (D) for preparing compounds of general formula (I) comprises the cyclisation of a compound of general formula (XI):

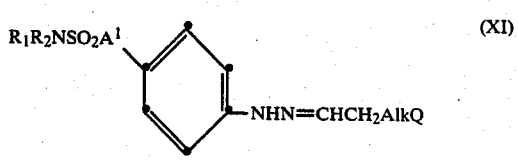

wherein Q is the group NR₃R₄ (or a protected derivative thereof) or a leaving atom or group such as a halogen atom (e.g. chlorine or bromine) or an acyloxy group, for example a carboxylic or sulphonic acyloxy group such as an acetoxy, chloroacetoxy, dichloroacetoxy, trifluoroacetoxy, p-nitrobenzoyloxy, p-toluenesulphonyloxy or methanesulphonyloxy group.

The reaction may conveniently be effected in aqueous or non-aqueous reaction media, and at temperatures of from 20° to 200° C., preferably 50° to 125° C.

Particularly convenient embodiments of the process are described below.

When Q is the group NR₃R₄ (or a protected derivative thereof) the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in an aqueous or non-aqueous reaction medium, in the presence of an acid catalyst. When an aqueous medium is employed this may be an aqueous organic solvent such as an aqueous alcohol (e.q. methanol, ethanol or isopropanol) or an aqueous ether (e.g. dioxan or tetrahydrofuran) as well as mixtures of such solvents and the acid catalyst may be, for example, an inorganic acid such as concentrated hydrochloric or sulphuric acid or an organic acid such as acetic acid. (In some cases the acid catalyst may also act as the reaction solvent). In an anhydrous reaction medium, which may comprise one or more ethers (e.g. as previously described) or esters (e.g. ethyl acetate), the acid catalyst will generally be a Lewis acid such as boron trifluoride, zinc chloride or magnesium chloride.

When Q is a leaving atom or group such as a chlorine or bromine atom the reaction may be effected in an aqueous organic solvent, such as an aqueous alcohol (e.g. methanol, ethanol or isopropanol) or an aqueous ether (e.g. dioxan or tetrahydrofuran) in the absence of an acid catalyst, conveniently at a temperature of from 20° to 200° l C., preferably 50° to 125° C. This process results in the formation of a compound of formula (I) wherein $R_3$ and $R_4$ are both hydrogen atoms.

According to a particular embodiment of this process compounds of formula (I) may be prepared directly by the reaction of a compound of general formula (XII):

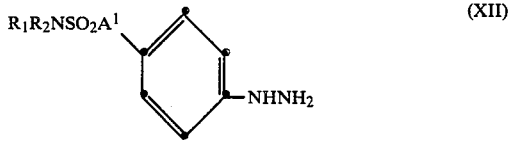
(XII)

or a salt thereof, with a compound of formula (XIII):

$$OHCCH_2AlkQ \qquad (XIII)$$

wherein Q is as defined above or a salt or protected derivative thereof (such as an acetal or ketal e.g. formed with an appropriate alkyl orthoformate or diol, or protected as a bisulphite addition complex) using the appropriate conditions as described above for the cyclisation of compounds of general formula (XI). It will be appreciated that in this embodiment of the cyclisation process (D) a compound of general formula (XI) is formed as an intermediate, and may be reacted in situ to form the desired compound of general formula (I).

Compounds of general formula (XI) may, if desired, be isolated as intermediates during the process for the preparation of compounds of formula (I) wherein a compound of formula (XII), or a salt or protected derivative thereof, is reacted with a compound of formula (XIII) or a salt or protected derivative thereof, in a suitable solvent, such as an aqueous alcohol (e.g. methanol) at a temperature of, for example, 20° to 30° C. If an acetal or ketal of a compound of formula (XIII) is used, it may be necessary to carry out the reaction in the presence of an acid (for example, acetic or hydrochloric acid).

Compounds of general formula (XII) may be prepared for example from the corresponding nitro compounds, using conventional procedures.

A further general process (E) for preparing compounds of general formula (I) involves reacting a compound of general formula (XIV):

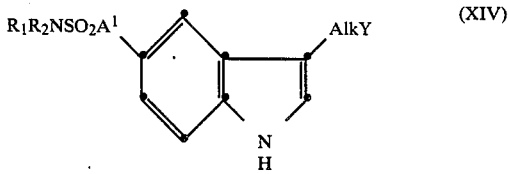
(XIV)

(wherein Y is a readily displaceable atom or group) or a protected derivative thereof, with an amine of formula $R_3R_4NH$.

The displacement reaction may conveniently be carried out on those compounds of formula (XIV) wherein the substituent Y is a leaving atom or group such as a halogen atom (e.g. chlorine, bromine or iodine) or a group $OR_7$ where $OR_7$ is, for example, an acyloxy group which may be derived from a carboxylic or sulphonic acid, such as an acetoxy, chloroacetoxy, dichloroacetoxy, trifluoroacetoxy, p-nitrobenzoyloxy, p-toluenesulphonyloxy or methanesulphonyloxy group.

The displacement reaction may be conveniently effected in an inert organic solvent (optionally in the presence of water), examples of which include alcohols, e.g. ethanol; cyclic ethers, e.g. dioxan or tetrahydrofuran; acylic ethers e.g. diethylether; esters, e.g. ethyl acetate; amides, e.g. N,N-dimethylformamide; and ketones e.g. acetone or methylethylketone, at a temperature of from $-10°$ to $+150°$ C., preferably 20° to 50° C.

The compounds of general formula (XIV) wherein Y is a halogen atom may be prepared by conventional procedures in which a hydrazine of general formula (XII) is reacted with an aldehyde or ketone (or a protected derivative thereof) of formula (XIII) in which Q is a halogen atom, in an aqueous alkanol (e.g. methanol) containing an acid (e.g. acetic or hydrochloric acid). Compounds of formula (XIV) wherein Y is the group $OR_7$ may be prepared from the corresponding compound wherein Y is a hydroxyl group by acylation with the appropriate activated species (e.g. anhydride or sulphonyl chloride) using conventional techniques. The intermediate alcohol may be prepared by cyclisation of a compound of formula (XI) wherein Q is a hydroxyl group (or a protected derivative thereof) under standard conditions.

Compounds of general formula (I) may also be prepared by another general process (F) which comprises reacting an indole of general formula (XV):

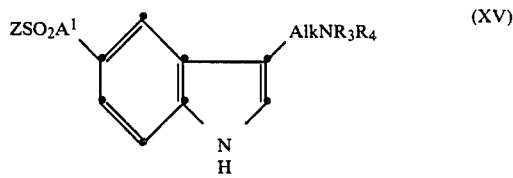
(XV)

wherein Z represents a leaving atom or group with a compound of general formula (XVI):

(XVI)

Examples of suitable leaving atoms or groups Z in the compound of general formula (XVI) include a halogen atom (e.g. a fluorine, chlorine or bromine atom) or a group $OR_8$ where $R_8$ represents a hydrocarbyl group such as an aryl group, e.g. phenyl. The aryl group may be unsubstituted or substituted by one or more substituents such as halogen atoms; or nitro; cyano; amino; alkyl e.g. methyl; alkoxy e.g. methoxy; acyl e.g. acetyl and alkoxycarbonyl e.g. ethoxycarbonyl groups. The leaving group represented by Z is preferably a phenoxy group.

The reaction is conveniently carried out in the presence of a solvent and may be effected in an aqueous or non-aqueous reaction medium.

The reaction medium may thus comprise one or more organic solvents, such as ethers, e.g. dioxan or tetrahydrofuran; amides e.g. N,N-dimethylformamide or N-methylpyrrolidone; alcohols e.g. methanol or ethanol;

esters e.g. ethyl acetate, nitriles e.g. acetonitrile; halogenated hydrocarbons e.g. dichloromethane; and tertiary amines e.g. triethylamine or pyridine, optionally in the presence of water. In some cases the amine of formula (XVI) may itself serve as the solvent.

If desired the aminolysis may be effected in the presence of a base, such as a tertiary amine (e.g. triethylamine or pyridine); an alkoxide (e.g. potassium t-butoxide); a hydride (e.g. sodium hydride); or an alkali metal carbonate (e.g. sodium carbonate).

The reaction may conveniently be effected at a temperature of from −20° C. to +150° C.

The starting materials of general formula (XV) may be prepared for example by cyclisation of a compound of general formula (XVII):

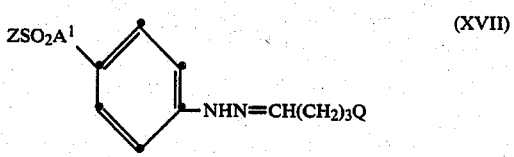

(wherein Z and Q are as previously defined).

The cyclisation may be effected in an analogous manner to the general process (D), described above.

According to a further general process (G) a compound of formula (I) according to the invention, or a salt or protected derivative thereof, may be converted into another compound of formula (I) using conventional procedures.

For example, a compound of general formula (I) wherein one or more of $R_1$, $R_2$, $R_3$ and $R_4$ are alkyl groups may be prepared from the corresponding compounds of formula (I) wherein one or more of $R_1$, $R_2$, $R_3$ and $R_4$ represent hydrogen atoms, by reaction with a suitable alkylating agent such as a compound of formula $R_xL$, (where $R_x$ represents the desired $R_1$, $R_2$, $R_3$ or $R_4$ group and L represents a leaving atom or group such as a halogen atom or a tosylate group) or a sulphate $(R_x)_2SO_4$. Thus, the alkylating agent may be for example an alkyl halide (e.g. methyl or ethyl iodide), alkyl tosylate (e.g. methyl tosylate) or dialkylsulphate (e.g. dimethylsulphate).

The alkylation may conveniently be carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides such as sodium or potassium hydride; alkali metal amides such as sodium amide; alkali metal carbonates such as sodium carbonate; alkali metal alkoxides such as sodium or potassium methoxide, ethoxide or t-butoxide; and tetrabutylammonium fluoride. When an alkyl halide is employed as the alkylating agent the reaction may also be carried out in the presence of an acid scavenging agent such as propylene or ethylene oxide. The reaction may be conveniently effected at a temperature of from −20° to 100° C.

Compounds of formula (I) wherein $R_1$ represents an alkenyl group, $R_2$ represents an alkenyl, phenylalkyl or cycloalkyl group and/or one or both of $R_3$ and $R_4$ represents propenyl may be prepared similarly, using an appropriate compound of formula $R_xL$ or $(R_x)_2SO_4$.

According to another general process (H), a compound of general formula (I) according to the invention, or a salt thereof may be prepared by subjecting a protected derivative of general formula (I) or a salt thereof to reaction to remove the protecting group or groups.

Thus, at an earlier stage in the reaction sequence for the preparation of a compound of general formula (I) or a salt thereof it may have been necessary or desirable to protect one or more sensitive groups in the molecule to avoid undesirable side reactions. For example it may be necessary to protect the group $NR_3R_4$, wherein $R_3$ and/or $R_4$ represents hydrogen, by protonation or with a group easily removable at the end of the reaction sequence. Such groups may include, for example, aralkyl groups, such as diphenylmethyl or triphenyl; or acyl groups such as N-benzyloxycarbonyl or t-butoxycarbonyl or phthaloyl.

Subsequent cleavage of the protecting group or groups may be achieved by conventional procedures. Thus an aralkyl group such as triphenylmethyl may be cleaved by treatment with dilute acid e.g. dilute hydrochloric acid; and an acyl group such as N-benzyloxycarbonyl may be removed by hydrolysis with, for example, hydrogen bromide in acetic acid.

The phthaloyl group may be removed by hydrazinolysis (e.g. by treatment with hydrazine hydrate) or by treatment with a primary amine (e.g. methylamine).

As will be appreciated, in some of the general processes (A) to (G) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (G).

Thus, according to a further aspect of the invention, the following reactions in any appropriate sequence may if necessary and/or desired be carried out subsequent to any of the processes (A) to (G):

(i) removal of any protecting groups; and
(ii) conversion of a compound of general formula (I) or a salt thereof into a physiologically acceptable salt or solvate (e.g. hydrate) thereof.

Where it is desired to isolate a compound of the invention as a salt, for example as an acid addition salt, this may be achieved by treating the free base of general formula (I), with an appropriate acid, preferably with an equivalent amount or with creatinine sulphate in a suitable solvent (e.g. aqueous ethanol).

The starting materials or intermediate compounds for the preparation of the compounds according to this invention may be prepared for example by analogous methods to those described in UK Published Patent Application Nos. 2035310 and 2124210.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following Examples. All temperatures are in °C. Chromatography was carried out either in the conventional manner using silica gel (Merck, Kieselgel 60, Art. 7734) or by flash chromatography (W. C.. Still, M. Kahn and A. Mitra, J. Org. Chem. 2933, 43, 1978) on silica (Merck 9385) and thin layer chromatography (t.l.c) on silica (Macherly-Nagel, Polygram) except where otherwise stated. The following abbreviations define the eluent used for chromatography and t.l.c.

(A) Methylene chloride-ethanol-0.88 ammonia 50:8:1
(B) Methylene chloride-ethanol-0.88 ammonia 100:8:1
(C) Methylene chloride-ether 1:1
(D) Methylene chloride-ethanol-0.88 ammonia 200:8:1
(E) Cyclohexane-ether 2:1
(F) Cyclohexane-ether 1:1

Intermediates were routinely checked for purity by t.l.c employing u.v. light for detection and spray reagents such as potassium permanganate ($KMnO_4$). In addition indolic intermediates were detected by spraying with aqueous ceric sulphate ($Ce^{IV}$) and tryptamines by spraying with a solution of iodoplatinic acid (IPA) or ceric sulphate.

Proton ($^1H$) nuclear magnetic resonance (n.m.r) spectra were obtained either at 90 MHz using a Varian EM 390 instrument or at 250 MHz using a Bruker AM or WM 250 instrument, s=singlet, d=doublet, t=triplet, m=multiplet and q=quartet.

Reactivials are 4 ml stout-walled glass vials with a screw cap and teflon-faced disc, supplied by Pierce and Warriner (UK) Ltd.

PREPARATION 1

N-Methyl-2-propenesulphonamide

Dry methylamine gas was bubbled through a solution of 2-propenesulphonyl chloride (5.24 g) in dry ether (50 ml) whilst maintaining the internal temperature at −78°. After 30 min, the flow of methylamine was stopped and the reaction mixture stirred at −78° for an additional period of 45 min. On allowing to warm to ambient temperature, water (100 ml) was added and the reaction mixture acidified (5N HCl; to pH1). The ethereal layer was separated and the aqueous phase extracted with dichloromethane (5×100 ml). The combined organic extracts were dried ($Na_2SO_4$) and concentrated in vacuo to afford the title compound as an oil (1.41 g)

T.l.c. (C) Rf 0.65.

N.m.r. $\delta(CDCl_3)$ 2.80(3H, d, $SO_2NHMe$), 3.72(2H, d, $CH_2SO_2NH$), 5.3–6.2 (3H, m, $CH_2=CH$).

PREPARATION 2

N-(2-Phenylethyl)ethenesulphonamide

2-Chloroethanesulphonyl chloride (8.15 g) was dissolved in benzene (30 ml), the solution cooled to 5°, stirred well and treated with 2-phenylethylamine (20 g) in benzene (12.5 ml). The mixture was stirred for a further 1 h, then washed with dilute hydrochloric acid (25 ml) and sodium hydrogen carbonate (8%, 50 ml) and dried to give an oil (10.3 g). This oil was distilled to give the product as an oil (2.2 g) which was then further purified by flash chromatography (E) to give the title compound (1.63 g) as an oil. T.l.c. (F) Rf 0.3 ($KMnO_4$).

PREPARATION 3

N-Cyclopentylethenesulphonamide

A mixture of cyclopentylamine (8.5 g) and triethylamine (27.8 ml) in ether (50 ml) was added dropwise over 6.5 h to a stirred solution of 2-chloroethanesulphonyl chloride (16.2 g) in anhydrous ether (200 ml) at ca−65°. The mixture was allowed to reach 15° over a period of 1 h, the suspension filtered and the filtrate concentrated in vacuo to give an oil (10.5 g), which was purified by chromatography (dichloromethane). A portion of the resulting oil (1.5 g) was distilled at 135°/6 mmHg to give the title compound (1.2 g) as an oil. T.l.c. (dichloromethane) Rf 0.5 ($KMnO_4$)

PREPARATION 4

N-[(4-Methoxyphenyl)methyl]ethenesulphonamide

A cold solution of 4-methoxybenzylamine (2 g) and triethylamine (2.8 ml) in dry dichloromethane (20 ml) at −78° was transferred under nitrogen to a solution of 2-chloroethanesulphonyl chloride (4.9 g) in dry dichloromethane (20 ml) at −78°. The mixture was stirred for 4 h whilst warming to room temperature and then refrigerated overnight. Water (ca 100 ml) was added and the organic layer separated. This was washed with hydrochloric acid (2N, 50 ml), water (50 ml) and brine (50 ml), dried ($MgSO_4$) and evaporated under reduced pressure. The residue was purified by chromatography (dichloromethane) to give the title compound as a powder (2 g) m.p. 68°–69°.

PREPARATION 5

4-[[(Ethenylsulphonyl)amino]methyl]benzamide

A solution of 4-aminomethylbenzamide (0.58 g) and triethylamine (1.1 ml) in dimethylformamide (DMF; 6 ml) was added to a solution of 2-chloroethanesulphonyl chloride (0.63 g) in DMF (4 ml) at −60° under nitrogen over 30 mins. The mixture was allowed to warm to room temperature and stirred for 18 h. The mixture was evaporated to give a semi-solid (2.78 g) which was purified by column chromatography (D) to give the title compound as a solid (0.54 g) m.p. 142°–4°.

Assay Found: C, 50.0; H, 5.3; N, 11.5. $C_{10}H_{12}N_2O_3S$ requires C, 50.0; H, 5.0; N, 11.7%.

PREPARATION 6

5-Iodo-N,N-dimethyl-1H-indole-3-ethanamine oxalate (i) 4-(dimethylamino)butanone (4-iodophenyl)hydrazone A solution of 4-iodophenylhydrazine (2 g) in water (70 ml) and 2N hydrochloric acid (4 ml) was stirred at room temperature with 4-dimethylaminobutanal, diethyl acetal (2.6 g) for 3 h. The resulting solution was partitioned between sodium bicarbonate (50 ml) and ethyl acetate (2×50 ml). The combined organic extracts were dried ($Na_2SO_4$) and evaporated in vacuo to give an oil (2.3 g), which was used directly in the next stage.

T.l.c. (B) Rf 0.3.

(ii) 5-Iodo-N,N-dimethyl-1H-indole-3-ethanamine oxalate

A solution of the product of Stage (i) (2.3 g) and polyphosphate ester (40 g) in chloroform (80 ml) was refluxed for 5 min. The solution was added to ice (300 g), stirred for 20 min, poured into 2N aqueous sodium carbonate (100 ml) and extracted with chloroform (2×100 ml). The combined organic extracts were dried ($Na_2SO_4$) and evaporated in vacuo. The resulting oil was purified by flash chromatography (B) to give pure free base as a solid. A solution of the base (0.92 g) in ethanol (20 ml) was added to oxalic acid (0.28 g) in methanol (5 ml) and the title compound precipitated. m.p. 176°–177°.

T.l.c. (B) Rf 0.3.

Analysis Found: C, 41.6; H, 4.2; N, 6.9. $C_{12}H_{15}IN_2.C_2H_2O_4$ requires C, 41.3; H, 4.1; N, 6.55%.

EXAMPLE 1

(E)-3-[3-[2-(Dimethylamino)ethyl]-1H-indol-5-yl]-N-methyl-2-propenesulphonamide oxalate A mixture of the product of Preparation 1 (247 mg), 5-bromo-N,N-dimethyl-1H-indole-3-ethanamine oxalate (650 mg), palladium acetate (8.3 mg), tri-ortho-tolylphosphine (26.3 mg) and triethylamine (1.05 ml) in acetonitrile (3 ml) was heated in a "reactivial" at 105°–110° for a period of 24 h. On cooling to ambient temperature, the reaction mixture was poured into water (20 ml) and the emulsion extracted with ethyl acetate (3×50 ml). The combined organic extracts were dried ($Na_2SO_4$) and concentrated in vacuo. Flash chromatography (B) of the residue afforded the free base as a foam (283 mg).

A filtered solution of the free base (272.5 mg) in absolute ethanol (0.5 ml) was added to a solution of oxalic acid (76.3 mg) in absolute ethanol (0.75 ml) from which a solid was deposited on scratching. The salt was filtered off (240 mg), washed with ether (20 ml) dried and recrystallised from ethanol (20 ml) to afford the title compound as a powder (98 mg) m.p. 93°–95°.

N.m.r. $\delta(CD_3SOCD_3)$ includes 2.66(3H, s, $SO_2NH$-Me), 2.81(6H, s, $NMe_2$), 3.05-3.3(4H, m, $CH_2CH_2N$), 3.96(2H, d, $SO_2CH_2CH=CH$), 6.15(1H, dt, $CH_2CH=CH$), 6.88(1H, d, $CH_2CH=CH$), 7.2-7.7(4H, m, aromatic).

EXAMPLE 2

The following compounds were prepared using a similar method to that in Example 1, the appropriate alkenesulphonamide and the reaction conditions shown in Table I.

(a)
(E)-2-[3-[2-(Dimethylamino)ethyl]-1H-indol-5-yl]ethenesulphonamide oxalate m.p. 192° (dec).

Analysis Found: C, 49.4; H, 5.5; N, 10.5. $C_{14}H_{19}N_3O_2S.C_2H_2O_4.0.44H_2O$ requires C, 49.1; H, 5,6; N, 10.7%.

N.m.r. $\delta(CD_3SOCD_3)$2.85(6H, s, $NMe_2$), 3.1-3.35(4H, m, $CH_2CH_2N$), 7.15(1H, d, $SO_2CH=CH$), 7.43(1H, d, $SO_2CH=CH$), 7.3-8.0(4H, m, aromatic).

(b)
(E)-2-[3-[2-(Dimethylamino)ethyl]-1H-indol-5-yl]-N-methylenesulphonamide oxalate m.p. 189°-190°.

Analysis Found: C, 50.95; H, 6.2; N, 10.45. $C_{15}H_{21}N_3O_2S.C_2H_2O_4.0.21H_2O$ requires C, 50.9; H, 5.9; N, 10.5%.

N.m.r. $\delta(CD_3SOCD_3)$2.83(6H, s, $NMe_2$)3.05-3.35(4H, m, $CH_2CH_2N$), 7.01(1H, d, $SO_2CH=CH$), 7.45(1H, d, $SO_2CH=CH$), 7.3-8.0(5H, m, aromatic+$NHSO_2$).

(c)
(E)-2-[3-[2-(Dimethylamino)ethyl]-1H-indol-5-yl]-N,N-dimethyl ethenesulphonamide oxalate m.p. 136°-138°.

Analysis Found: C, 51.6; H, 6.0; N, 9.5. $C_{16}H_{23}N_3O_2S.C_2H_2O_4.0.53H_2O.0.33C_2H_6O$ C, 51.4; H, 6.4; N, 9.6%.

N.m.r. $\delta(CD_3SOCD_3)$2.75(6H, s, $SO_2NMe_2$), 2.84(6H, s, $NMe_2$), 3.05-3.35(4H, m, $CH_2CH_2N$), 7.15(1H, d, $SO_2CH=CH$), 7.51(1H, d, $SO_2CH=CH$), 7.3-8.05(4H, m, aromatic).

(d)
(E)-2-[3-[2-(Dimethylamino)ethyl]-1H-indol-5-yl]-N-(2-phenylethyl)ethenesulphonamide hemifumarate m.p. 186°-189°.

Analysis Found: C, 62.6; H, 6.4; N, 9.0. $C_{22}H_{27}N_3O_2S.0.5C_4H_4O_4.0.013H_2O$ C, 62.9; H, 6.4; N, 9.2%.

N.m.r. $\delta(CD_3SOCD_3)$2.27(6H, s, $NMe_2$), 2.56(2H, m, $CH_2NMe_2$), 2.75-2.9(4H, m, $CH_2CH_2N$ and $PhCH_2CH_2$), 3.16(2H, m, $CH_2NHSO_2$), 6.9(1H, d, $SO_2CH=CH$), 7.15-7.9 (10H, m, aromatic+N-$HSO_2CH=CH$).

(e) (E)-2-[3-[2-(Dimethylamino)ethyl]-1H-indol-5-yl]-N-(1-methylethyl)ethenesulphonamide oxalate m.p. 125°-129°.

Analysis Found: C, 53.1; H, 6.5; N, 9.8. $C_{17}H_{25}N_3O_2.C_2H_2O_4.0.12H_2O$ requires C, 53.4; H, 6.4; N, 9.8%.

N.m.r. $\delta(CD_2SOCD_3)$1.12(6H, d, $CHMe_2$), 2.79(6H, s, $NMe_2$), 3.05-3.2(4H, m, $CH_2CH_2N$), 3.37(1H, m, $CHMe_2$), 7.02(1H, d, $SO_2CH=CH$), 7.3-8.0(5H, m, aromatic+$SO_2CH=CH$).

(f)
(E)-2-[3-[2-(Dimethylamino)ethyl]-1H-indol-5-yl]-N-ethylenesulphonamide hemifumarate m.p. 200°-201°.

Analysis Found: C, 56.3; H, 6.7; N, 10.7. $C_{16}H_{23}N_3O_2S.0.5C_4H_4O_4.0.15H_2O$ requires C, 56.6; H, 6.6; N, 11.0%.

N.m.r. $\delta(CD_3SOCD_3)$1.10(3H, t, $SO_2NHCH_2CH_3$), 2.40(6H, s, $NMe_2$), 2.7-3.0 (6H, m, $CH_2CH_2N$ and $SO_2NHCH_2CH_3$), 7.01(1H, d, $SO_2CH=CH$), 7.25-7.95 (5H, m, aromatic+$SO_2CH=CH$).

(g)
(E)-N-Cyclopentyl-2-[3-[2-(dimethylamino)ethyl]-1H-indol-5-yl]ethenesulphonamide oxalate m.p. 202°-203°.

Analysis Found: C, 55.1; H, 6.5; N, 9.1. $C_{19}H_{27}N_3O_2S.C_2H_2O_4.0.27H_2O$ requires C, 55.3; H, 6.4; N, 9.2%.

N.m.r. $\delta(CD_3SOCD_3)$1.4-1.9(8H, m, cyclopentylmethylene protons), 2.83(6H, s, $NMe_2$), 3.05-3.35(4H, m, $CH_2CH_2N$), 3.55(1H, m, $SO_2NHCH$), 7.02(1H, d, $SO_2CH=CH$), 7.3-8.0(5H, m, aromatics+$SO_2CH=CH$).

(h)
(E)-2-[3-[2-(Dimethylamino)ethyl]-1H-indol-5-yl]-N-phenylethene sulphonamide hemioxalate m.p. 203°-205° (d).

Analysis Found: C, 59.4; H, 5.7; N, 9.4. $C_{20}H_{23}N_3O_2S.0.5C_2H_2O_4.0.5H_2O.0.25EtOH$ requires C, 59.1; H, 6.1; N, 9.6%.

N.m.r. $\delta(CD_3SOCD_3)$2.53(6H, s, $NMe_2$)2.8-3.0(4H, m, $CH_2CH_2N$), 7.0-8.0 (12H, m, aromatics+$SO_2CH=CH-+2NH$).

(i)
(E)-2-[3-[2-(Dimethylamino)ethyl]-1H-indol-5-yl]-N-[(4-methoxyphenyl)methyl]ethenesulphonamide oxalate m.p. 166°–169°.

Analysis Found: C, 57.1; H, 6.0; N, 8.2 $C_{22}H_{27}N_3O_3S \cdot C_2H_4O_4$ requires: C, 57.2; H, 5.8; N, 8.3%.

a solution of anhydrous oxalic acid (51.4 mg) in absolute ethanol (0.50 ml), and on scratching a crystalline material was deposited. The salt was filtered off, dried and recrystallised from absolute ethanol (5 ml) to afford the title compound as an amorphous powder (80 mg).

m.p. 141°–143° (softens 131°).

Analysis Found: C, 52.1; H, 6.6; N, 9.95. $C_{16}H_{25}N_3O_2S \cdot C_2H_2O_4$ requires C, 52.3; H, 6.6; N, 10.2%.

TABLE I

Example 2

| | FORMATION OF BASE | | | | | SALT FORMATION | | | |
|---|---|---|---|---|---|---|---|---|---|
| Compound | sulphonamide (g) | Indole (g) | Temp. (°C.) | Time (h) | Yield (g) | Base (g) | Acid (g) | Solvent | Yield (g) |
| a | 0.196 | 0.65 | 100–110 | 24 | 0.237 | 0.211 | oxalic 0.065 | EtOH | 0.18 |
| b | 0.40 | 1.0 | 100 | 66 | 0.8 | 0.3 | oxalic 0.09 | EtOH | 0.1 |
| c | 0.44 | 1.17 | 100 | 24 | 0.39 | 0.16 | oxalic 0.045 | EtOH | 0.04 |
| d | 0.69 | 0.8 | 100 | 24 | 0.45 | 0.10 | fumaric 0.015 | EtOAc | 0.056 |
| e | 0.65 | 0.273 | 120 | 17 | 0.43 | 0.153 | oxalic 0.041 | EtOH | 0.147 |
| f | 0.44 | 1.17 | 100 | 24 | 0.66 | 0.10 | fumaric 0.018 | EtOAc | 0.093 |
| g | 0.57 | 1.17 | 100 | 24 | 0.55 | 0.11 | oxalic 0.027 | EtOAc | 0.075 |
| h | 0.74 | 0.74 | 110 | 16 | 0.38 | 0.097 | oxalic 0.024 | EtOH | 0.025 |
| i | 0.25 | 0.39 | 100 | 24 | 0.16 | 0.16 | oxalic 0.036 | EtOAc | 0.175 |

EtOH = Ethanol
EtOAc = Ethyl acetate

EXAMPLE 3

4-[[[[2-[3-[2-(Dimethylamino)ethyl]-1H-indol-5-yl]ethenyl]sulphonyl]amino]methyl]benzamide oxalate A mixture of 5-iodo-N,N-dimethyl-1H-indole-3-ethanamine, oxalate (0.65 g), 4-[[(ethenylsulphonyl)amino]methyl]benzamide (0.40 g), palladium acetate (16 mg) and triethylamine (0.7 ml) in methanol (4 ml) was heated in a 5 ml "reacti-vial" at 100° for 22 h. The mixture was evaporated to give an oil (1.65 g) which was purified by column chromatography (B) to give a solid (245 mg). This was dissolved in methanol (2 ml) and a solution of oxalic acid (52 mg) in methanol (2 ml) was added. The mixture was evaporated to give a foam (288 mg) which was recrystallised from ethanol/toluene and combined with similarly prepared material to afford the title compound as a solid, (312 mg), m.p. 145°–150°.

Analysis Found: C, 56.4; H, 5.4; N, 9.7. $C_{24}H_{28}N_4O_7S \cdot 0.10$ EtOH. 0.32 mol toluene requires C, 57.65; H, 5.8; N, 10.2%.

EXAMPLE 4

3-[2-(Dimethylamino)ethyl]-N-methyl-1H-indole-5-propanesulphonamide oxalate

A solution of the product of Example 1 (237.5 mg) in absolute ethanol (20 ml) was hydrogenated over prereduced 10% palladium oxide (450 mg, 50% aqueous paste) at ambient temperature and pressure for a period of 24 h. The reaction mixture was filtered through a celite-sand pad, which was washed thoroughly with ethanol (100 ml) and the combined filtrates concentrated in vacuo. Flash chromatography (A) of the residue afforded the product as an oil (184.5 mg), which was dissolved in absolute ethanol (1 ml) and filtered through a cotton wool plug. To this solution was added N.m.r. δ(CD₃SOCD₃) 1.98 (2H, m, CH₂CH₂CH₂SO₂NH) 2.53 (d, MeNHSO₂), 2.83 (6H, s, NMe₂), 2.7–3.35 (8H, m, CH₂CH₂NMe₂ and CH₂CH₂CH₂SO₂NH), 6.85–7.45 (5H, m, aromatic+N-HSO₂).

EXAMPLE 5

The following compounds were prepared according to the method of Example 4, using the starting materials and reaction conditions given in Table II below.

(a)

3-[2-(Dimethylamino)ethyl]-1H-indole-5-ethanesulphonamide oxalate m.p. 176°–178°.

Analysis Found: C, 49.45; H, 5.9; N, 10.6. $C_{14}H_{21}N_3O_2S \cdot C_2H_2O_4 \cdot 0.32H_2O$ requires C, 49.1; H, 6.1; N, 10.7%.

N.m.r. δ(CD₃SOCD₃) 2.86 (6H, s, NMe₂), 3.0–3.4 (8H, m, CH₂CH₂SO₂NH₂ and CH₂CH₂NMe₂), 6.85–7.55 (6H, m, aromatic+SO₂NH₂).

(b)

3-[2-(Dimethylamino)ethyl]-N-methyl-1H-indole-5-ethanesulphonamide

N.m.r. (CD₃OD) 2.42 (6H, s, NMe₂), 2.74 (5H, s, MeNHSO₂ and m, CH₂CH₂NMe₂), 2.98 (2H, CH₂CH₂NMe₂), 3.16–3.44 (4H, m, CH₂CH₂SO₂NHMe), 7.0–7.5 (4H, m, aromatic).

(c)

3-[2-(Dimethylamino)ethyl]-N,N-dimethyl-1H-indole-5-ethanesulphonamide oxalate m.p. 130°–135°.

Analysis Found: C, 51.4; H, 6.8; N, 9.8. $C_{16}H_{25}N_3O_2S.C_2H_2O_4.0.26H_2O$ requires C, 51.7; H, 6.6; N, 10.05%.

N.m.r. $\delta(CD_3SOCD_3)$ 2.81 (12H, s, $Me_2NSO_2$ and $CH_2NMe_2$), 3.0–3.4 (8H, m, $Me_2NSO_2CH_2CH_2$ and $CH_2CH_2NMe_2$), 7.0–7.55 (4H, m, aromatic).

(d)
3-[2-(Dimethylamino)ethyl]-N-(2-phenylethyl)-1H-indole-5-ethanesulphonamide oxalate m.p. 155°–156°.

Analysis Found: C, 58.5; H, 6.4; N, 8.3. $C_{22}H_{29}N_3O_2S.C_2H_2O_4.0.08H_2O$ requires C, 58.7; H, 6.4; N, 8.6%.

N.m.r. $\delta(CD_3SOCD_3)$ 2.82 (6H, s, $NMe_2$), 2.75–3.35 (12H, m, $—CH_2CH_2NMe_2$ and $—CH_2CH_2N-HSO_2CH_2CH_2—$), 6.95–7.5 (10H, m, aromatic+N-$HSO_2$).

(e)
3-[2-(Dimethylamino)ethyl]-N-(1-methylethyl)-1H-indole-5-ethanesulphonamide oxalate m.p. 168°–170°.

Analysis Found: C, 53.3; H, 6.8; N, 9.6. $C_{17}H_{27}N_3O_2S.C_2H_2O_4.0.1H_2O$ requires C, 53.2; H, 6.8; N, 9.8%.

N.m.r. $\delta(CD_3SOCD_3)$ 1.16 (6H, d, $CHMe_2$), 2.82 (6H, s, $NMe_2$), 3.0–3.35 (8H, m, $CH_2CH_2NMe_2$ and $NHSO_2CH_2CH_2$), 6.98–7.5 (5H, aromatic+$NHSO_2$)

(f)
3-[2-(Dimethylamino)ethyl]-N-ethyl-1H-indole-5-ethanesulphonamide oxalate m.p. 158°–159°.

Analysis Found: C, 52.1; H, 6.5; N, 10.5. $C_{16}H_{25}N_3O_2S.C_2H_2O_4.0.03H_2O$ requires C, 52.2; H, 6.6; N, 10.1%.

N.m.r. $\delta(CD_3SOCD_3)$ 1.12 (3H, t, $MeCH_2NHSO_2$), 2.95–3.35 (10H, m, $MeCH_2NHSO_2CH_2CH_2$ and $CH_2CH_2NMe_2$), 7.0–7.55 (5H, m, aromatic+$NHSO_2$).

(g)
N-Cyclopentyl-3-[2-(dimethylamino)ethyl]-1H-indole-5-ethanesulphonamide oxalate m.p. 181°–182°.

Analysis Found: C, 55.4; H, 7.0; N, 8.9. $C_{19}H_{29}N_3O_2S.C_2H_2O_4$ requires C, 55.5; H, 6.9; N, 9.2%.

N.m.r. $\delta(CD_3SOCD_3)$ 1.4–1.96 (8H, m, cyclopentyl $CH_2 \times 4$) 2.83 (6H, s, $NMe_2$), 3.0–3.36 (8H, m, $SO_2CH_2CH_2$ and $CH_2CH_2NMe_2$), 3.65 (1H, m, $SO_2NHCH$) 6.98–7.52 (4H, m, aromatics).

(h)
3-[2-(Dimethylamino)ethyl]-N-[(4-methoxyphenyl)methyl]-1H-indole-5-ethanesulphonamide oxalate m.p. 142°–144°.

Analysis Found: C, 55.9; H, 6.2; N, 8.0. $C_{22}H_{29}N_3O_3S.C_2H_4O_4.0.5H_2O$ requires: C, 56.0; H, 6.3; N, 8.2%.

N.m.r. $\delta(CD_3SOCD_3)$ 2.83 (6H, s, $NMe_2$), 2.9–3.35 (8H, m, $CH_2CH_2SO_2NH$ and $CH_2CH_2NMe_2$), 3.75 (3H, s, OMe), 4.15 (2H, d, $CH_2NHSO_2$), 6.8–7.45 (8H, m, aromatic).

TABLE II

| | Starting Material | | Example 5 Hydrogenation | | | Salt Formation | | |
|---|---|---|---|---|---|---|---|---|
| Compound | Product of Ex. No. | Weight (g) | PdO/C (g) | Time (h) | Yield of base (g) | oxalic acid (g) | Solvent | Yield (g) |
| a | 2a | 0.14 | 0.28 | 14 | 0.085 | 0.026 | EtOH | 0.053 |
| b | 2b | 0.056 | 0.11 | 6 | 0.045 | — | — | — |
| c | 2c | 0.25 | 0.95 | 18 | 0.22 | 0.010 | EtOAc | 0.040 |
| d | 2d | 0.31 | 0.60 | 18 | 0.137 | 0.031 | (1) EtOAc (2) EtOH | 0.040 |
| e | 2e | 0.755 | 2.0 | 19 | 0.255 | 0.068 | EtOH | 0.274 |
| f | 2f | 0.56 | 0.9 | 18 | 0.20 | 0.030 (× 2) | EtOH + MeOH | 0.221 |
| g | 2g | 0.40 | 0.8 | 6h | 0.234 | 0.051 | EtOH | 0.080 |
| h | 2i | 0.59 | 0.6 | — | 0.45 | 0.10 | (1) EtOAc + MeOH + E (2) EtOH | 0.25 |

EtOH = Ethanol
EtOAc = Ethyl acetate
MeOH = Methanol
E = Diethyl ether

EXAMPLE 6

3-[2-(Dimethylamino)ethyl]-N-phenyl-1H-indole-5-ethanesulphonamide hemioxalate

A solution of the product of Example 2 h (283 mg) in absolute alcohol (30 ml) was hydrogenated over pre-reduced 10% palladium oxide on charcoal (740 mg, 50% aqueous paste pre-reduced in ethanol, 20 ml) for a period of 18 h at room temperature and pressure. The mixture was filtered through a sand-celite pad, which was thoroughly washed with ethanol (150 ml). The filtrate was concentrated in vacuo and the residue was taken up in ethanol (30 ml) and treated with Raney nickel (~50 mg) for a period of 30 min. The Raney nickel was removed by filtration, and the filtrate rehydrogenated for a further 18 h. The catalyst was removed by filtration through a sand-celite pad and the filtrate concentrated in vacuo. Flash chromatography (A) of the residue afforded the product as a low melting solid (103 mg). A filtered solution of the solid in warm absolute ethanol (2 ml) was added to an ethanolic solution of anhydrous oxalic acid (25 mg in 1 ml). On scratching, an amorphous solid was deposited, which was filtered off, air dried (1 h) and recrystallized from ethanol (30 ml) to afford the title compound as an amorphous powder, m.p. 144°–146°.

Analysis Found: C, 58.9; H, 6.6; N, 9.0. $C_{20}H_{25}N_3O_2S.0.5C_2H_2O_4.0.4C_2H_6O0.7H_2O$ requires C, 58.5; H, 6.7; N, 9.4%.

N.m.r. $\delta(CD_3SOCD_3)$ 2.63 (6H, s, $NMe_2$) 2.98 (4H, m, $CH_2CH_2NMe_2$), 3.06 (2H, m, $SO_2CH_2CH_2$), 3.38 (2H, m, $SO_2CH_2CH_2$), 6.8–7.5 (9H, m, aromatics).

The following examples illustrate pharmaceutical formulations according to the invention, containing (E)-2-[3-[2-(dimethylamino)ethyl]-1H-indol-5-yl]-N-[(4- methoxyphenyl)methyl]ethenesulphonamide oxalate as the active ingredient. Other compounds of the invention may be formulated in a very similar manner.

TABLETS FOR ORAL ADMINISTRATION

| DIRECT COMPRESSION | mg/tablet |
|---|---|
| Active ingredient | 2.4 |
| Calcium hydrogen phosphate B.P.* | 95.10 |
| Croscarmellose sodium USP | 2.00 |
| Magnesium stearate, B.P. | 0.50 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| CAPSULES | mg/capsule |
|---|---|
| Active ingredient | 2.4 |
| *Starch 1500 | 196.6 |
| Magnesium Stearate BP | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP | mg/5 ml dose |
|---|---|
| Active ingredient | 2.4 |
| Buffer | |
| Flavour | |
| Colour | |
| Preservative | as required |
| Thickening agent | |
| Sweetening agent | |
| Purified Water to | 5.00 ml |

The active ingredient, buffer, flavour, colour, preservative, thickening agent and sweetening agent are dissolved in some water, the solution is adjusted to volume and mixed. The syrup produced is clarified by filtration.

| SUPPOSITORY FOR RECTAL ADMINISTRATION | |
|---|---|
| Active ingredient | 2.4 mg |

| -continued | |
|---|---|
| SUPPOSITORY FOR RECTAL ADMINISTRATION | |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

| INJECTION FOR INTRAVENOUS ADMINISTRATION | mg/ml |
|---|---|
| Active ingredient | 0.6 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. Indoles of the formula (I):

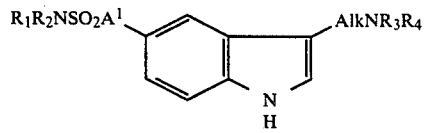

wherein $R_1$ represents a hydrogen atoms or a $C_{1-6}$ alkyl or $C_{3-6}$ alkenyl group;

$R_2$ represents a hydrogen atom, a $C_{1-3}$ alkyl, $C_{3-6}$ alkenyl, or $C_{5-7}$ cycloalkyl group, or a phenyl or phenyl ($C_{1-4}$) alkyl group in which the phenyl ring is unsubstituted or substituted by a halogen atom, a $C_{1-3}$ alkyl, $C_{1-3}$ alkoxy or hydroxyl group, or by a group —$NR_aR_b$, or —$CONR_aR_b$, wherein $R_a$ and $R_b$, which may be the same or different, each represents a hydrogen atom or a $C_{1-3}$ alkyl or $C_{3-6}$ alkenyl group, or together with the nitrogen atom to which they are attached form a saturated monocyclic 5 to 7-membered ring or a saturated monocyclic 5 to 7-membered ring containing an additional oxygen atom or group $NR_5$, where $R_5$ is a hydrogen or a $C_{1-3}$ alkyl; $R_3$ and $R_4$, which may be the same or different, each represents a hydrogen atom or a $C_{1-3}$ alkyl or propenyl group or $R_3$ and $R_4$ together form an aralkylidene benzylidene group;

Alk represents an alkyl chain containing two or three carbon atoms which may be unsubstituted or substituted by not more than two $C_{1-3}$ alkyl groups; and $A^1$ represents an alkenyl chain containing two to five carbon atoms, and physiologically acceptable salts and solvates thereof.

2. Indoles according to claim 1, wherein $A^1$ represents a group

—(CH$_2$)$_m$CH=CH(CH$_2$)$_n$— wherein m is zero or an integer from 1 to 3 and n is zero or an integer from 1 to 3 and the sum of m and n does not exceed 3.

3. Indoles according to claim 1, represented by the formula (I')

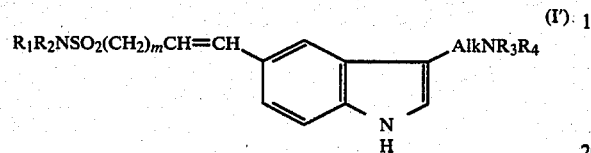

wherein

R$_1$, R$_2$, R$_3$, R$_4$ and Alk are as defined in claim 1 and m is zero or an integer from 1 to 3, and physiologically acceptable salts and solvates thereof.

4. Indoles according to claim 1, wherein Alk represents an unsubstituted alkyl chain containing two carbon atoms.

5. Indoles according to claim 1, in the E-configuration with regard to the double bond in the 5-substituent.

6. Indoles according to claim 1, of the formula (Ia):

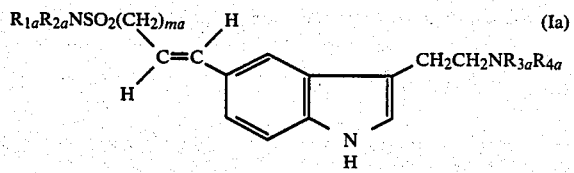

wherein
- R$_{1a}$ represents a hydrogen atom or a C$_{1-3}$ alkyl group;
- R$_{2a}$ represents a hydrogen atom, a C$_{1-3}$ alkyl group or a phenyl or phenyl(C$_{1-2}$) alkyl group in which the phenyl ring is unsubstituted or substituted by a C$_{1-3}$ alkoxy group or by the group —CONH$_2$;
- R$_{3a}$ and R$_{4a}$ each represents a hydrogen atom or a C$_{1-3}$ alkyl group; and
- ma is zero or 1;

and physiologically acceptable salts and solvates thereof.

7. Indoles according to claim 1, selected from the group consisting of (E)-2-[3-[2-(dimethylamino)ethyl]-1H-indol-5-yl]-N-methylethenesulphonamide;

(E)-2-[3-[2-(dimethylamino)ethyl]-1Hindol-5-yl]-N-(2-phenylethyl)ethenesulphonamide;

(E)-2-[3-[2-(dimethylamino)ethyl]-1H-indol-5-yl]-N-[(4-methoxyphenyl)methyl]ethenesulphonamide;

and the physiologically acceptable salts and solvates thereof.

8. A pharmaceutical composition for treating or preventing pain resulting from dilation of the cranial vasculaure which comprises as active ingredient an effective amount of at least one indole of general formula (I) according to claim 1 or a physiologically acceptable salt or solvate thereof together with one or more pharmaceutically acceptable carriers or excipients.

* * * * *